(12) United States Patent
Main et al.

(10) Patent No.: US 7,356,120 B2
(45) Date of Patent: Apr. 8, 2008

(54) INTEGRATED QUALITY ASSURANCE FOR IN IMAGE GUIDED RADIATION TREATMENT DELIVERY SYSTEM

(75) Inventors: William Main, Aptos, CA (US); Eric Earnst, Saratoga, CA (US); Gopinath Kuduvalli, San Jose, CA (US)

(73) Assignee: Accuray Incorporated, Sunnyvale, CA (US)

(*) Notice: Subject to any disclaimer, the term of this patent is extended or adjusted under 35 U.S.C. 154(b) by 4 days.

(21) Appl. No.: 11/234,708

(22) Filed: Sep. 23, 2005

(65) Prior Publication Data

US 2007/0071176 A1    Mar. 29, 2007

(51) Int. Cl.
*A61N 5/10* (2006.01)

(52) U.S. Cl. .................. 378/65; 378/205; 378/207; 250/252.1

(58) Field of Classification Search ................ 378/65, 378/163, 205, 207; 250/252.1; 33/286, 33/533
See application file for complete search history.

(56) References Cited

U.S. PATENT DOCUMENTS

| | | | |
|---|---|---|---|
| 1,252,550 A | 1/1918 | Champney | |
| 5,193,106 A * | 3/1993 | DeSena | 378/163 |
| 6,267,502 B1 * | 7/2001 | McNeirney et al. | 378/206 |
| 6,516,046 B1 * | 2/2003 | Frohlich et al. | 378/65 |
| 6,528,803 B1 | 3/2003 | Ritt | |
| 6,529,575 B1 * | 3/2003 | Hsieh | 378/4 |
| 6,675,116 B1 | 1/2004 | Ritt | |
| 7,056,019 B1 * | 6/2006 | Hanson et al. | 378/207 |
| 7,197,830 B2 * | 4/2007 | Vaccaro | 33/286 |
| 2002/0085668 A1 * | 7/2002 | Blumhofer et al. | 378/68 |
| 2004/0042583 A1 * | 3/2004 | Wackerle et al. | 378/65 |
| 2005/0080332 A1 * | 4/2005 | Shiu et al. | 600/411 |
| 2006/0239414 A1 * | 10/2006 | Foulquier et al. | 378/207 |

FOREIGN PATENT DOCUMENTS

FR    2854050 A1 * 10/2004

OTHER PUBLICATIONS

Low et al., Minimization of target positioning error in accelerator-based radiosurgery, Medical Physics, 22, (4), pp. 443-448, Apr. 1995.*
PCT/US06/36620, Written Opinion of the International Searching Authority (United States), dated May 14, 2007.

(Continued)

*Primary Examiner*—Edward J. Glick
*Assistant Examiner*—John M Corbett
(74) *Attorney, Agent, or Firm*—Blakely, Sokoloff, Taylor & Zafman LLP

(57) ABSTRACT

A method and apparatus for quality assurance of an image guided radiation treatment delivery system. A quality assurance ("QA") marker is positioned at a preset position under guidance of an imaging guidance system of a radiation treatment delivery system. A radiation beam is emitted from a radiation source of the radiation treatment delivery system at the QA marker. An exposure image of the QA marker due to the radiation beam is generated. The exposure image is then analyzed to determine whether the radiation treatment delivery system is aligned.

18 Claims, 8 Drawing Sheets

OTHER PUBLICATIONS

PCT/US06/36620, International Search Report (United States), dated Jun. 7, 2007.

"Dynamic Phantom," CIRS Model 008 Dynamic Thorax Phantom Specifications, pp. 53-54.

"Anthropomorphic Phantoms," Radiological Physics Center. Retrieved from http://rpc.mdanderson.org/rpc/services/Anthropomorphic_%20Phantoms/Anth_SRS.htm (Retrieved on Mar. 28, 2007).

"Instructions for SRS Quality Audit System," Radiological Physics Center. Retrieved from http://rpc.mdanderson.org/rpc/services/Anthropomorphic_%20Phantoms/SRSInstrucForInst.pdf (Retrieved on Mar. 28, 2007).

Yu, Cheng Ph.D. et al., "An Anthropomorphic Phantom Study of the Accuracy of CyberKnife Spinal Radiosurgery," NEUROSURGERY, vol. 55, No. 5, Nov. 2004, pp. 1138-1149.

* cited by examiner

ALIGNMENT

MISALIGNMENT

INTEGRATED QUALITY ASSURANCE FOR IN IMAGE GUIDED RADIATION TREATMENT DELIVERY SYSTEM

TECHNICAL FIELD

This disclosure relates generally to quality assurance for image guided radiation treatment delivery systems.

BACKGROUND INFORMATION

In radiosurgery, very intense and precisely collimated doses of radiation in a beam from a source outside a patient's body are delivered to a target region in the body, in order to destroy lesions. Typically, the target region consists of a volume of tumorous tissue. Radiosurgery requires an extremely accurate spatial localization of the targeted lesions. Radiosurgery offers apparent advantages over conventional surgery, during which a surgeon's scalpel removes the lesion, by avoiding the common risks and problems associated with open surgery. These problems include invasiveness, high costs, the need for in-hospital stays and general anesthesia, and complications associated with post-operative recovery. When a lesion is located close to critical organs, nerves, or arteries, the risks of open surgery are even greater.

As a first step in performing radiosurgery, it is necessary to determine with great precision the location of lesion and any surrounding critical structures, relative to the reference frame of the treatment device. Computed tomography ("CT"), magnetic resonance imaging ("MRI") scans, and other imaging modalities enable practitioners to precisely locate a lesion relative to skeletal landmarks or implanted fiducial markers. However, it is also necessary to control the position of the radiation source so that its beam can be precisely directed to the target tissue while avoiding adjacent critical body structures.

Thus radiosurgery necessitates high precision diagnosis and high precision radiation source control. The consequences of deviating outside the prescribed tolerances for the diagnosis and the radiation source control can be potentially devastating to a patient. Accordingly, quality assurance mechanisms should be integrated into a radiation treatment delivery system to ensure proper alignment and configuration of the system prior to delivering a prescribed radiation dose to a patient.

Conventional quality assurance mechanisms include pointing the radiation source at an alignment marker, delivering a radiation dose to the alignment marker, and then analyzing the alignment marker itself to determine if the prescribed dose was actually delivered to the correct location. If the prescribed dose was delivered as expected, then the radiation treatment delivery system is deemed properly aligned. If the prescribed dose was not delivered as expected, then the radiation treatment delivery system is deemed misaligned. Conventional alignment markers include silver loaded gels capsules or photographic film canisters that can store readable information about the distribution of the radiation dose delivered to the alignment marker. However, extracting this alignment information from silver loaded gels or photographic film canisters located within the alignment marker itself is a time consuming and costly task.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system and method for quality assurance of an image guided radiation treatment delivery system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
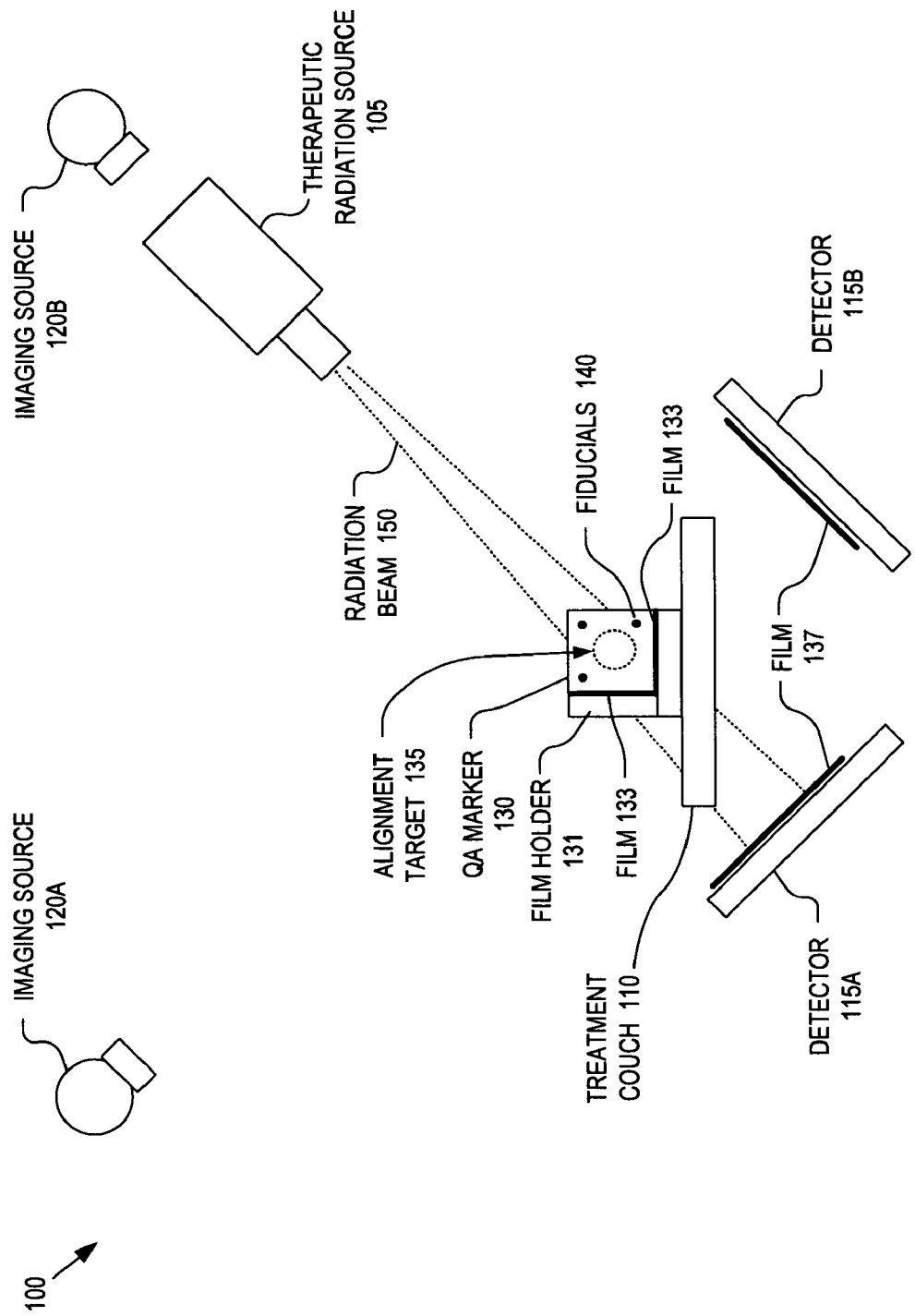
FIG. 1 is a diagram illustrating use of a quality assurance marker to execute an alignment confidence check of an image guided radiation treatment system, in accordance with an embodiment of the invention.

FIG. 1 is a diagram illustrating use of a quality assurance ("QA") marker to execute an alignment confidence check on a radiation treatment delivery system 100, in accordance with an embodiment of the invention. The illustrated embodiment of radiation treatment delivery system 100 includes a therapeutic radiation source 105, a treatment couch 110, detectors 115A and 115B (collectively 115, also referred to as imagers), and imaging sources 120A and 120B (collectively 120).

Radiation treatment delivery system 100 may be used to perform radiosurgery to treat or destroy lesions within a patient. During radiosurgery, the patient rests on treatment couch 110, the treatment couch is maneuvered to position the lesion or volume of interest ("VOI") to a preset position or within an operating range accessible to therapeutic radiation source 105 (e.g., field of view). In one embodiment, radiation treatment delivery system 100 is an image guided radiation treatment delivery system. Together, imaging sources 120 and detectors 115 are an imaging guidance system that provides visual control over the position of treatment couch 110 and the patient thereon. In one embodiment, treatment couch 110 may be coupled to a positioning system (e.g., robotic arm) that receives feedback from the imaging guidance system to provide accurate control over both the displacement and orientation of the VOI within the patient and therapeutic radiation source 105.

Prior to radiosurgery, it is important to execute quality assurance ("QA") mechanisms to ensure radiation treatment delivery system 100 is properly aligned and configured prior to delivery of a treatment dose of radiation to a patient. These QA mechanisms, also referred to as confidence checks, validate that the imaging system, the positioning system (not illustrated), treatment couch 110, and therapeutic radiation source 105 are all calibrated and aligned with each other.

A QA marker 130 may be placed on treatment couch 110 to perform one of these QA mechanisms. The illustrated embodiment of QA marker 130, commonly referred to as a "shadow phantom" for reasons described below, includes an alignment target 135 and fiducials 140. Fiducials 140 are used by the imaging guidance system to position QA marker 130 to a preset position. Subsequently, therapeutic radiation source 105 is also maneuvered into a preset position. From this preset position, therapeutic radiation source 105 emits a radiation beam 150 along a predetermined trajectory passing through QA marker 130 and impinging upon one of detectors 115 (illustrated as detector 115A). In response to radiation beam 150, a beam exposure field is produced or develops on detector 115A outlining a shadow cast by alignment target 135. By analyzing the relative positions of the shadow and the beam exposure field, alignment of therapeutic radiation source 105 can be validated or a misalignment exposed. In one embodiment, the amount of exposure in the beam exposure field may be analyzed to determine if the correct dose was delivered.

By emitting multiple radiation beams from different positions, one impinging on detector 115A and the other impinging on detector 115B, multi-dimensional alignment validation can be achieved. In one embodiment, QA marker 130 provides three-dimensional translational alignment validation. In one embodiment, QA marker 130 provides both three-dimensional translational alignment validation and rotational (e.g., roll, pitch, yaw) alignment validation. Translational/rotational alignment validation includes validating the ability of the imaging guidance system and the positioning system to achieve accurate translational/rotational placement of QA marker 130 at the preset position and the ability of therapeutic radiation source 105 to arrive at its translational/rotational preset position.

In one embodiment, the exposure image generated by propagating radiation beam 150 through QA marker 130 is captured by detectors 115. Detectors 115 may be implemented using digital imagers (e.g., PerkinElmer imager). Alternatively, the exposure image may be captured using film 137, such as standard (MD) radiochromic film, high-sensitivity ("HS") radiochromic film, and the like. In the embodiment using detectors 115 or films 137, therapeutic radiation source 105 may be aligned normal to detectors 115/films 137 such that the exposure images (and shadows) are cast onto detectors 115/films 137. In another embodiment, film holder 131 is used to hold films 133 adjacent to QA marker 130. In an embodiment using films 133, therapeutic radiation source 105 may be aligned normal to each film 133 prior to emitting radiation beam 150. It should be appreciated that if film holder 131 and films 133 are used to capture the exposure images, then films 137 need not be present, and visa versa. Furthermore, a variety of other positions/orientations of film and/or therapeutic radiation source 105 may be used to generate and capture exposure images of QA marker 130. The intensity, duration, and collimation of the radiation beam 150 (i.e., treatment dose), may be dependent upon the technique used to capture the exposure image (e.g., 30 Gy for MD radiochromic film, 10 Gy for HS radiochromic film, 200 Gy for EBT film, or 0.01 Gy for PerkinElmer imager). In an embodiment using film, the amount of exposure on the film may be analyzed and compared to determine whether the correct dose of radiation was delivered.

Figure 2A:
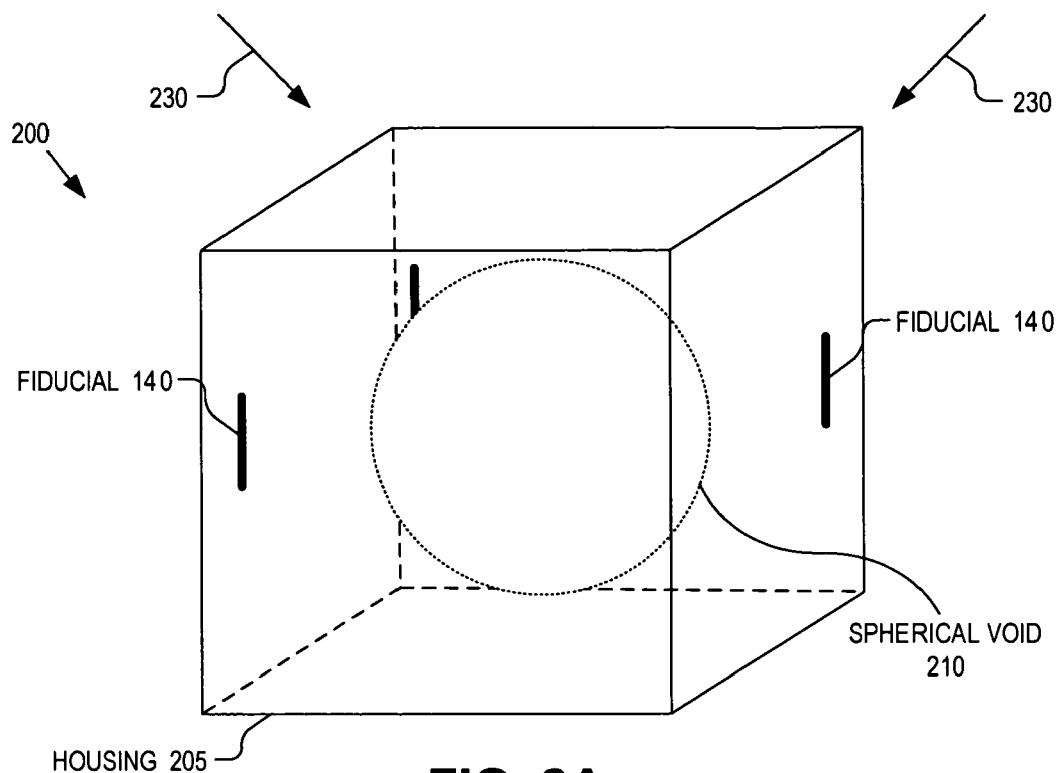
FIG. 2A is a perspective view illustrating a quality assurance marker for housing a spherical target for alignment validation of an image guided radiation treatment system, in accordance with an embodiment of the invention.

Alignment target 135 may be implemented with a variety of different sizes, shapes, orientations, and elements to cast simple symmetrical shadows onto detectors 115 or more complex non-symmetrical shapes. FIG. 2A is a perspective view illustrating a QA marker 200 for supporting a spherical target to validate alignment of radiation treatment delivery system 100, in accordance with an embodiment of the invention. QA marker 200 represents one possible embodiment of QA marker 130 illustrated in FIG. 1. The illustrated embodiment of QA marker 200 includes a housing 205 having a spherical void 210 for holding a spherical target 215 and fiducials 140. It should be appreciated that the size, shapes, and orientations of the various components of QA marker 200 are not illustrated to scale.

In one embodiment, housing 205 is formed of ABS plastic. However, housing 205 may be formed of a variety of materials being transparent or translucent to radiation beam 150. In one embodiment, housing 205 is also translucent or penetrable by the emissions of imaging sources 120. Although housing 205 is illustrated as a cube, housing 205 may assume any convenient shape.

Figure 2B:
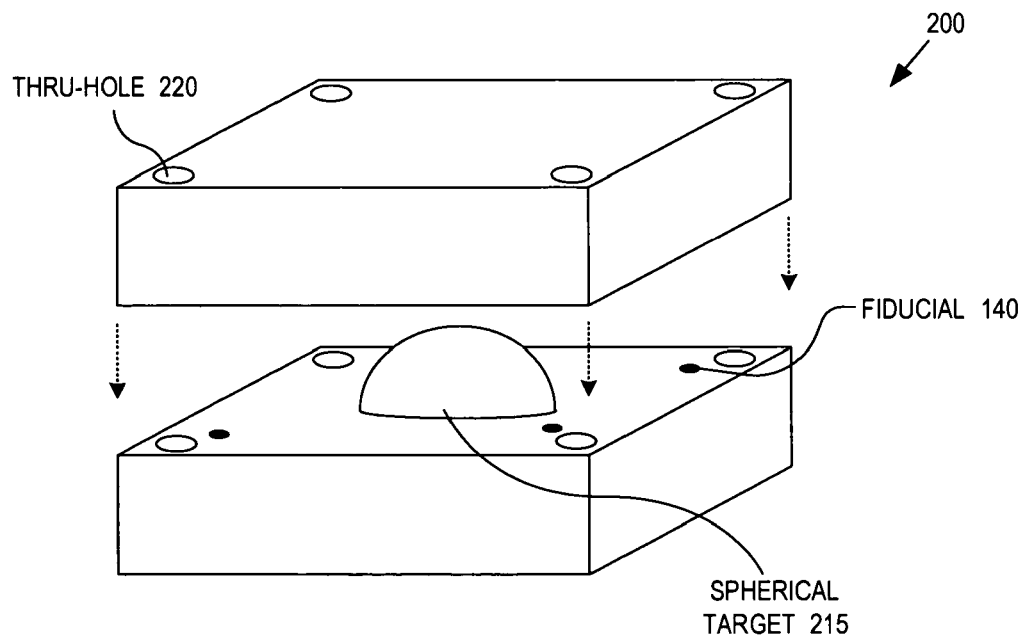
FIG. 2B is a perspective view illustrating a quality assurance marker opened to allow swapping of the spherical target, in accordance with an embodiment of the invention.

FIG. 2B is a perspective view illustrating a QA marker 200 opened to enable swapping of spherical target 215, in accordance with an embodiment of the invention. As illustrated, QA marker 200 may be formed of multiple separable portions (e.g., two or more). These portions may be secured with fasteners (e.g., plastic screws, bolts, pins, rivets, etc.) inserted into thru-holes 220. Embodiments of QA marker 200 are separable to support multiple imaging modalities compatible with different materials for spherical target 215. For example, if QA marker 200 is imaged with x-ray imaging sources, then a spherical target 215 formed of a radio opaque material (e.g., metal, metal alloy, etc.) may be inserted into spherical void 210. If QA marker 200 is imaged using a CT scanner, a spherical target 215 formed of acrylic may be inserted into spherical void 210. The particular material selected for spherical target 215 is dependent upon the imaging modality to provide sufficient image contrast. In one embodiment, housing 205 is approximately 2.5 inches square with a 1.25 inch diameter spherical void 210. Other sizes, shapes, and materials are possible.

In the illustrated embodiment, QA marker 200 includes three fiducials 140 embedded within housing 205 at three separate corners. Fiducials 140 are embedded within QA marker 200 to enable the imaging guidance system to track QA marker 200. In one embodiment, fiducials 140 are gold wires approximately 1 mm in diameter and 5 mm long. However, fiducials 140 may assume a variety of shapes, sizes, orientations, and positions that are convenient to track. Although three identical fiducials 140 are illustrated, more or less, similar or individually distinct fiducials 140 may be incorporated into housing 205 for tracking purposes. In one embodiment, housing 205 does not include any fiducials 140, but rather uses spherical target 215 itself for image tracking.

QA marker 200 may be exposed to one or more radiation beams 150 along one or more trajectories 230 to capture exposure images of QA marker 200 for validating system alignment. It should be appreciated that trajectories 230 may vary for various different embodiments. For example, trajectories 230 may include trajectories that are horizontal, vertical, normal to any of the sides of housing 205, or otherwise. These exposure images may be captured with therapeutic radiation source 105 having a variety of different separation distances from the center of alignment target 135 (referred to as source to axis distance "SAD"). For example the SAD may be equal to 650 mm, 800 mm, 950 mm, or otherwise.

Figure 3A:
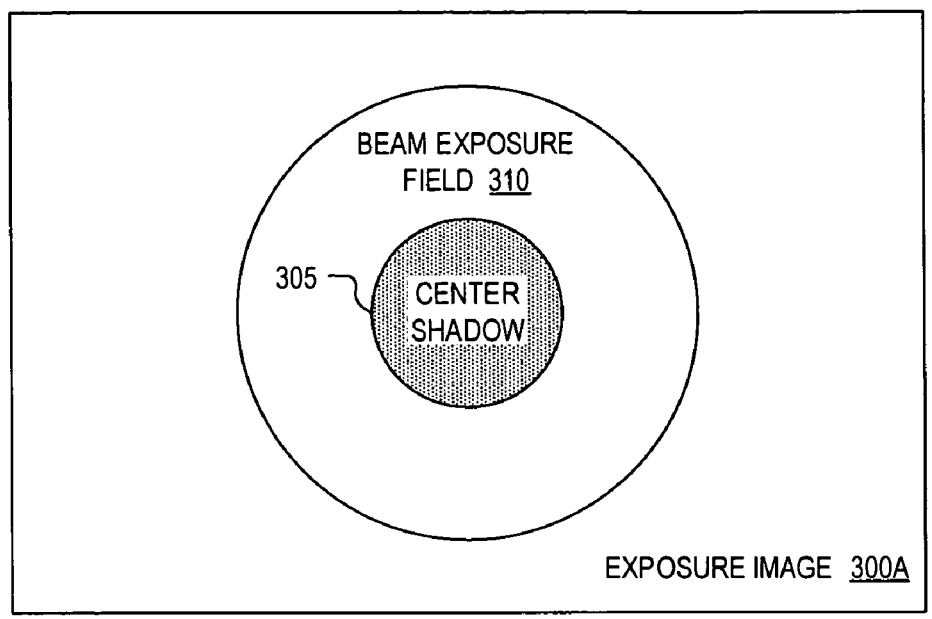
FIG. 3A is a diagram illustrating a target shadow and a beam exposure field having concentric centroids indicating alignment of a radiation treatment delivery system, in accordance with an embodiment of the invention.
Figure 3B:
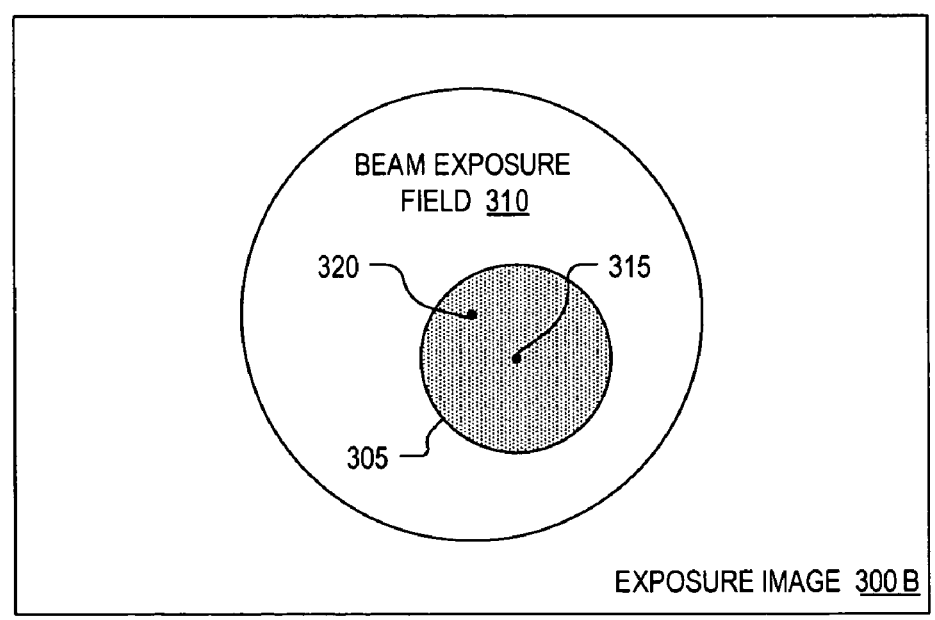
FIG. 3B is a diagram illustrating a target shadow and a beam exposure field having non-concentric centroids indicating misalignment of a radiation treatment delivery system, in accordance with an embodiment of the invention.

FIGS. 3A and 3B illustrate two possible exposure images 300A and 300B of QA marker 200. FIG. 3A is a diagram illustrating a center shadow 305 and a beam exposure field 310 having concentric centroids. The presence of concentrically aligned centroids in exposure image 300A indicates that radiation treatment delivery system 100 is properly aligned and calibrated (at least for the degrees of freedom tested by the particular image). In short, the presence of concentrically aligned centroids in exposure image 300A is a confidence check that the imaging guidance system and the positioning system were able to accurately place QA marker 200 at the preset position and that the therapeutic radiation source 105 was able to achieve its preset position.

FIG. 3B is a diagram illustrating center shadow 305 and beam exposure field 310 having non-concentric centroids 315 and 320, respectively. The presence of non-concentrically aligned centroids 315 and 320 in exposure image 300B indicates that radiation treatment delivery system 100 is misaligned. In short, the presence of non-concentrically aligned centroids 315 and 320 in exposure image 300B indicates that either the imaging guidance system or the positioning system did not accurately place QA marker 200 at the preset position or that the therapeutic radiation source 105 did not achieve its preset position.

In one embodiment, exposure images 300A and 300B may be captured (e.g., using a digital imager, film, etc.), imported into a software tool, and analyzed to pinpoint the centroids of center shadow 305 and beam exposure field 310. If the centroids overlap within a margin of error, then alignment is determined. If the centroids are displaced from each other, then misalignment is determined. This automated analysis is called stereotactic alignment. In one embodiment, a software product called RIT113 by Radiological Imaging Technology, Inc. of Colorado Springs, Colo. may be used in connection with embodiments of the invention to perform stereotactic alignment analysis.

Figure 4A:
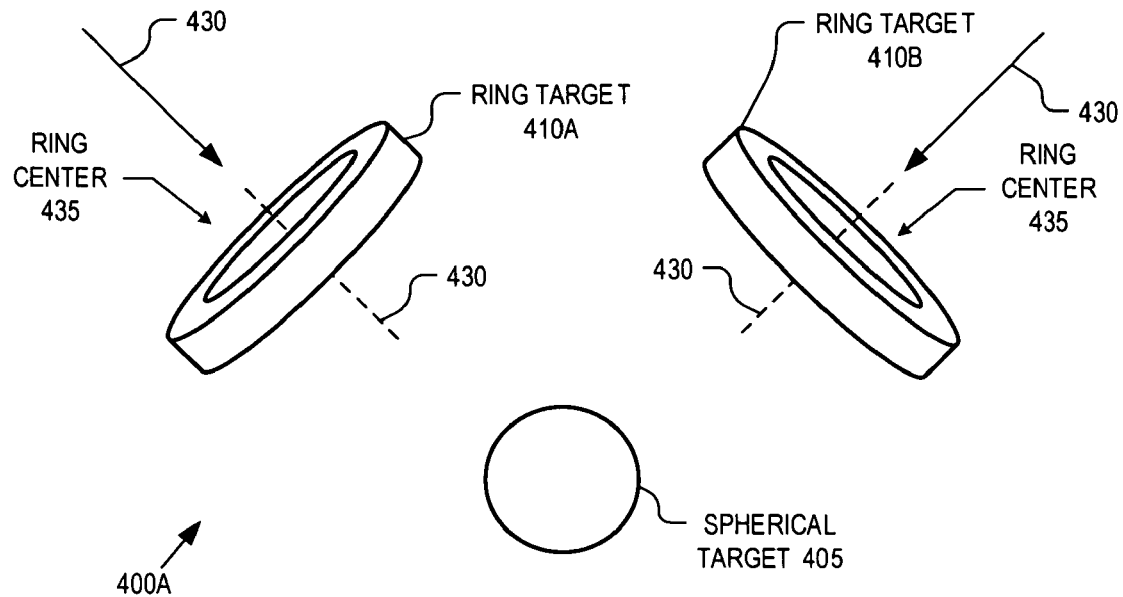
FIG. 4A is a perspective view of spherical and ring targets for use with a quality assurance marker to provide displacement and rotational validation of a radiation treatment delivery system, in accordance with an embodiment of the invention.
Figure 4B:
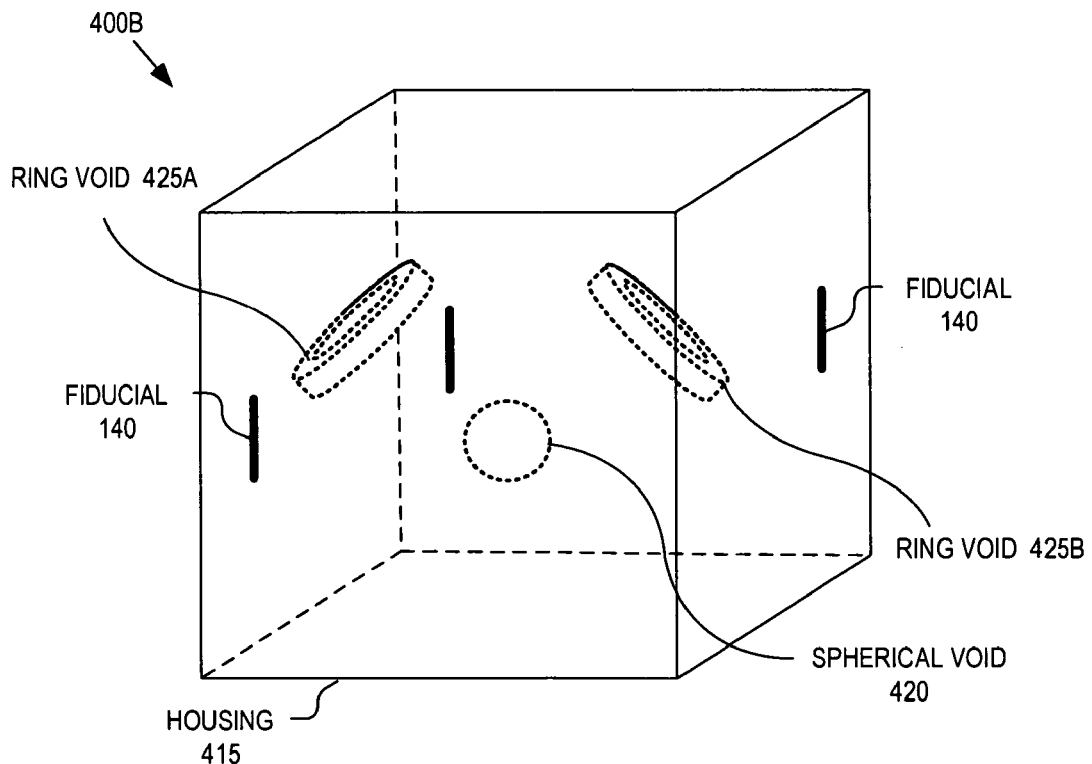
FIG. 4B is a perspective view illustrating a quality assurance marker for holding spherical and ring targets for validation of an image guided radiation treatment delivery system, in accordance with an embodiment of the invention.

FIGS. 4A and 4B illustrate an alignment target 400A for use with a QA marker 400B to provide displacement and rotational validation of radiation treatment delivery system 100, in accordance with an embodiment of the invention. Alignment target 400A is another possible embodiment of alignment target 135 and QA marker 400B is another possible embodiment of QA marker 130, illustrated in FIG. 1.

The illustrated embodiment of alignment target 400A includes a spherical target 405, and ring targets 410A and 410B (collectively 410). The illustrated embodiment of QA marker 400B includes a housing 415 including a spherical void 420, ring voids 425A and 425B (collectively 425), and fiducials 140. As with QA marker 200 illustrated in FIG. 2B, QA marker 400B may be formed of multiple separable portions (not illustrated) enabling alignment target 400A to be inserted/removed into/from housing 415. Depending upon the imaging modality used to view QA marker 400B, alignment marker 400A may be formed of a radio opaque material (e.g., metal) for imaging by therapeutic radiation source 105 or imaging sources 120, acrylic for CT imaging, or otherwise. In one embodiment, housing 415 is formed of ABS plastic or other materials being transparent or translucent to the various imaging modalities.

When alignment target 400A is inserted into housing 415, ring target 410A is supported within ring void 425A, ring target 410B is supported within ring void 425B, and spherical target 405 is supported within spherical void 420. Once positioned within housing 415, ring targets 410 are orientated such that ring axes 430 are substantially aligned with a trajectory passing through the center of spherical target 405. Ring centers 435 have an inside diameter that is larger than a diameter of spherical target 405.

Figure 5A:
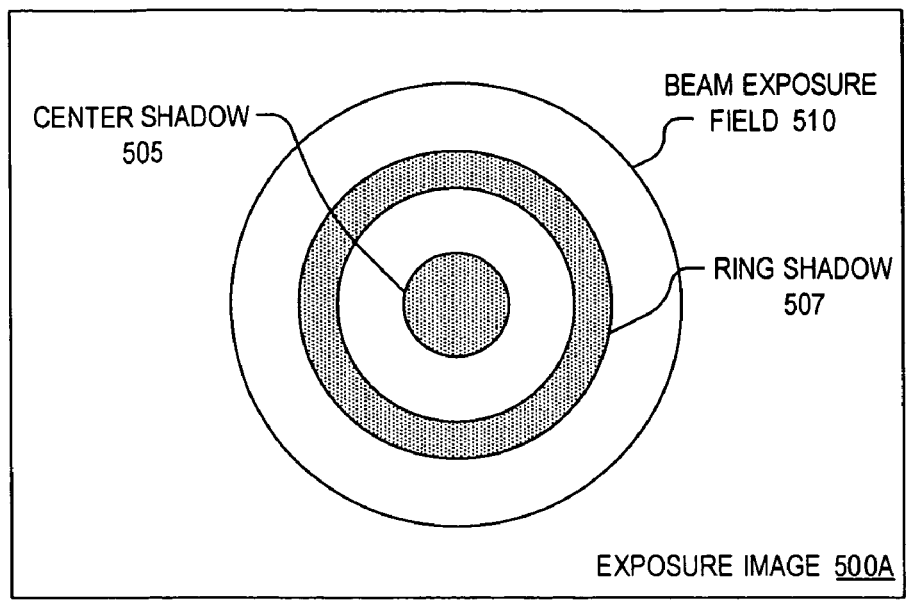
FIG. 5A is a diagram illustrating target shadows and a beam exposure field all having concentric centroids indicating alignment of a radiation treatment delivery system, in accordance with an embodiment of the invention.
Figure 5B:
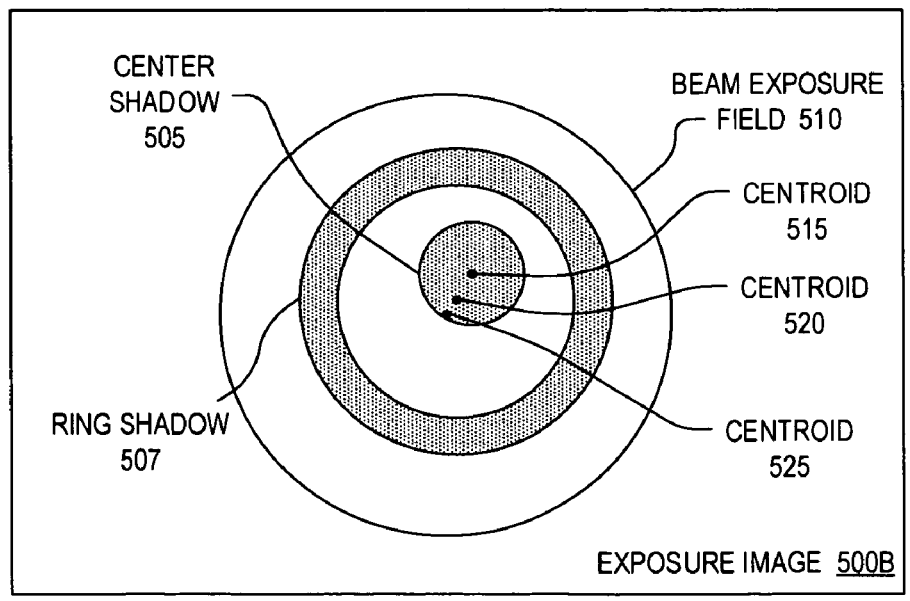
FIG. 5B is a diagram illustrating target shadows and a beam exposure field having non-concentric centroids indicating misalignment of a radiation treatment delivery system, in accordance with an embodiment of the invention.

QA marker 400B may be exposed to one or more radiation beams 150 along one or more trajectories 430 to capture exposure images of QA marker 400B for validating system alignment. FIGS. 5A and 5B illustrate two possible exposure images 500A and 500B of QA marker 400B. FIG. 5A is a diagram illustrating a center shadow 505, a ring shadow 507, and a beam exposure field 510 having concentric centroids. The presence of concentrically aligned centroids in exposure image 500A indicates that radiation treatment delivery system 100 is properly aligned and calibrated. In other words, exposure image 500A is a confidence check indicating that the imaging guidance system and the positioning system were able to accurately place QA marker 400B at the preset position and that the therapeutic radiation source 105 was able to achieve its preset position.

Alignment target 400A is capable of exposing both translational displacement error and rotational error. FIG. 5B is a diagram illustrating center shadow 505, ring shadow 507, and beam exposure field 510 having non-concentric centroids 515, 520, and 525, respectively. The presence of non-concentrically aligned centroids 515, 520, and 525 in exposure image 500B indicates that radiation treatment delivery system 100 is misaligned. In short, the presence of non-concentrically aligned centroids 515, 520, and 525 in exposure image 500B indicates that either the imaging guidance system and the positioning system did not accurately place QA marker 200 at the preset position or that the therapeutic radiation source 105 was did not achieve its preset position. Although not illustrated, a rotational misalignment may add distortions or warping to the various components of exposure image 500B. Accordingly, the presence of distortions, warping, or skewing of the target shadows or beam exposure field 510 is a further indicator that radiation treatment delivery system 100 is misaligned and therefore should be recalibrated prior to treating a patient.

Although only two configurations have been explicitly illustrated herein for QA marker 130, it should be appreciated that other shapes, dimensions, and materials may be implemented. For example, spherical targets 215 or 405 may be elongated, star shape, cross-shaped, T-shaped, X-shaped, or otherwise. Using a simple symmetrical shape alone, such as a sphere, simplifies computation of the centroid of its shadow, but may only provide displacement error detection. Adding additional simple shapes, such as ring targets 410, enable detection of both displacement and rotational errors with minimal increase in difficulty of centroid computation. A single more complicated shape may be used for both displacement and rotational error detection; however, the difficulty of computing the centroid of its shadow may correspondingly increase.

Figure 6:
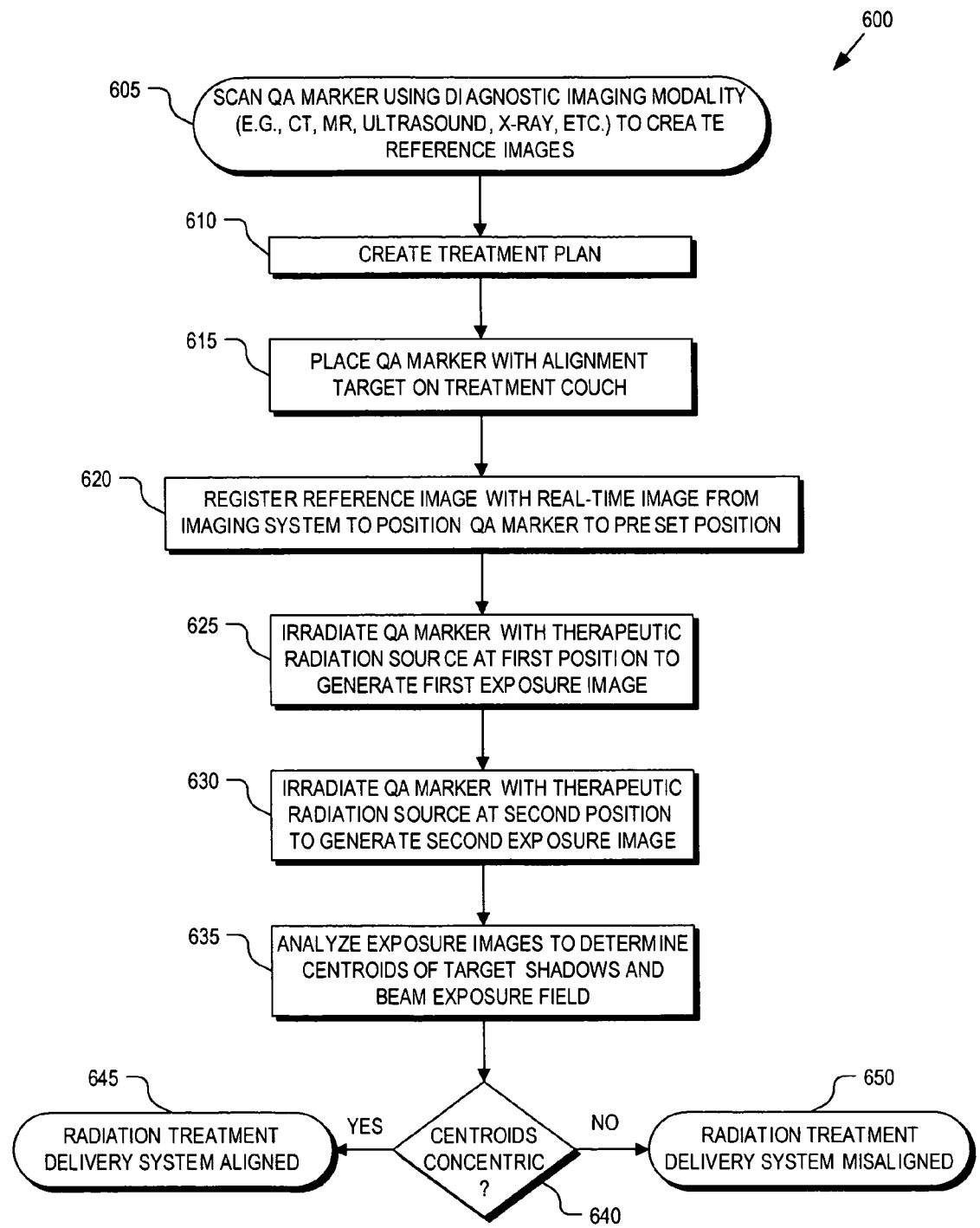
FIG. 6 is a flow chart illustrating a process to provide quality assurance of alignment between an imaging guidance system, a positioning system, and a therapeutic radiation source of a radiation treatment delivery system, in accordance with an embodiment of the invention.

FIG. 6 is a flow chart illustrating a process 600 to provide quality assurance of alignment between the imaging guidance system, the positioning system, and therapeutic radiation source 105 of radiation treatment delivery system 100, in accordance with an embodiment of the invention. The order in which some or all of the process blocks appear in process 600 should not be deemed limiting. Rather, one of ordinary skill in the art having the benefit of the present disclosure will understand that some of the process blocks may be executed in a variety of orders not illustrated.

In a process block 605, QA marker 130 is scanned using diagnostic imaging equipment to generate a reference image(s) of QA marker 130. A different imaging modality (e.g., CT scan, MRI, PET, ultrasound, x-ray, microwave, etc.) may be used to generate the reference images than is used by therapeutic radiation source 105 during the alignment test. Accordingly, a low density diagnostic alignment target 135 made of a material compatible with the diagnostic modality (e.g., acrylic for CT scans) may be inserted into QA marker 130.

In a process block 610, a treatment plan is generated based on the reference images. The treatment plan may include a determination of the preset positions and orientations for QA marker 130 and therapeutic radiation source 105, as wells as the dose to be delivered at each preset position during the alignment test.

In a process block 615, an operator of radiation treatment delivery system 100 places QA marker 130 onto treatment couch 110. Prior to placing QA marker 130 onto treatment couch 110 the low density diagnostic alignment target 135 may be swapped for the high density test alignment target 135 being made of a material compatible with therapeutic radiation source 105 (e.g., radio opaque material such as metal).

In a process block 620, the reference image(s) are loaded into a control system of radiation treatment delivery system 100. The reference images are registered to the real-time images captured by detectors 115 and imaging sources 120 (the imaging guidance system). In one embodiment, the imaging guidance system registers fiducials 140 from each of the two images. Using fiducials 140, the positioning system translates/rotates treatment couch 110 to position QA marker 130 into the preset position within the field of view or operating range of therapeutic radiation source 105 to be used during the alignment test. The positioning system places QA marker 130 into the preset position under the control of the imaging guidance system. In other embodiments, the alignment target 135 itself is used to track and place QA marker 130, without fiducials 140.

In a process block 625, therapeutic radiation source 105 moves to its first preset position and delivers a dose of radiation beam 150 through QA marker 130 onto detector 115A (or film positioned behind QA marker 130). Alignment target 135 casts a shadow onto detector 115A creating an exposure image of itself and radiation beam 150.

In a process block 630, therapeutic radiation source 105 moves to its second preset position and delivers a second dose of radiation beam 150 through QA marker 130 onto detector 115B (or film positioned behind QA marker 130). Alignment target 135 casts a shadow onto detector 115B creating another exposure image of itself and radiation beam 150.

In a process block 635, the two exposure images are imported into a computer and analyzed. In an embodiment using film, the film is first developed and then scanned into the computer for analysis. A software tool (e.g., RIT113 from Radiological Imaging technology, Inc.) may used to analyze the exposure images and determine the centroids of the shadows cast by alignment target 135 and the beam exposure field.

If the centroids are concentrically aligned in both exposure images (decision block 640), then radiation treatment delivery system 100 is deemed aligned (process block 645) and therefore ready for patient treatment delivery. However, if one of the exposure images includes non-concentrically aligned centroids, then radiation treatment delivery system 100 is deemed misaligned (process block 650) and therefore not ready for patient treatment delivery. In this case, the radiation treatment delivery system 100 should be recalibrated and then retested.

In an embodiment using digital images for detectors 115, the first exposure image may be uploaded directly into the analysis software once captured. If the analysis software determines that the centroids are not aligned, then the alignment test finishes without need of executing process block 630, since it will already be determined that radiation treatment delivery system 100 is misaligned. Furthermore, embodiments of the invention are not limited only to a determination whether target shadows and the beam exposure field are concentrically aligned. Rather, embodiments of the invention may include configurations where non-concentrically aligned shadow shapes indicate alignment. Further, embodiments of the invention are not limited to a determination of whether centroids are aligned. Rather, the analysis software may look for alignment between shadow boundaries or various other features to determine alignment.

In one embodiment, the two exposure images may also be analyzed for the amount of exposure within the beam exposure fields to determine whether therapeutic radiation source 105 delivered the correct dose of radiation. Analyzing for correct dose delivery may include comparing the exposure images against reference images to determine the dose of radiation delivered. In this case, the two exposure images are analyzed for overall system calibration, including both alignment verification and dose verification.

Figure 7:
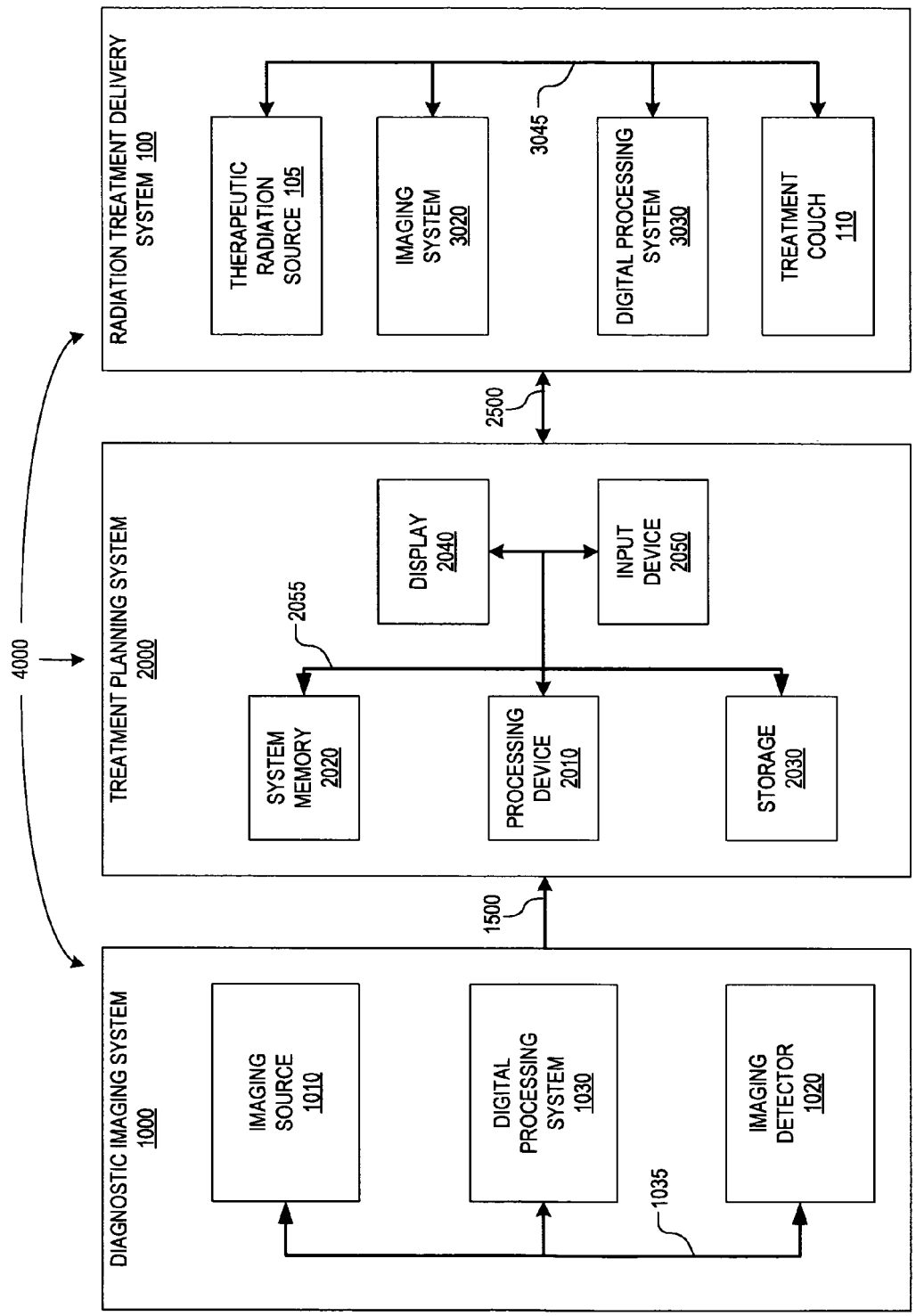
FIG. 7 is a block diagram illustrating a therapeutic patient treatment system for generating diagnostic images, generating a treatment plan, and delivering the treatment plan, in accordance with an embodiment of the invention.

FIG. 7 is a block diagram illustrating a therapeutic patient treatment system 4000 for generating diagnostic images, generating a treatment plan, and delivering the treatment plan to a patient, in which features of the present invention may be implemented. As described below and illustrated in FIG. 7, systems 4000 may include a diagnostic imaging system 1000, a treatment planning system 2000 and a radiation treatment delivery system 100.

Diagnostic imaging system 1000 may be any system capable of producing medical diagnostic images of a volume of interest ("VOI") in a patient that may be used for subsequent medical diagnosis, treatment planning and/or treatment delivery. For example, diagnostic imaging system 1000 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor ("DSP") or other type of device such as a controller or field programmable gate array ("FPGA"). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a DSP or other type of device such as a controller or FPGA. Processing device 2010 may be configured to execute instructions for performing treatment planning operations discussed herein.

Treatment planning system 2000 may also include system memory 2020 that may include a random access memory ("RAM"), or other dynamic storage devices, coupled to processing device 2010 by bus 2055, for storing information and instructions to be executed by processing device 2010. System memory 2020 also may. be used for storing temporary variables or other intermediate information during execution of instructions by processing device 2010. System memory 2020 may also include a read only memory ("ROM") and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube ("CRT") or liquid crystal display ("LCD"), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as radiation treatment delivery system 100, so that it may not be necessary to export from the treatment planning system prior to treatment delivery. Treatment planning system 2000 may be linked to radiation treatment delivery system 100 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or radiation treatment delivery system 100 may be in decentralized locations such that the systems may be physically remote from each other. Alternatively, any of diagnostic imaging system 1000, treatment planning system 2000 and/or radiation treatment delivery system 100 may be integrated with each other in one or more systems.

Radiation treatment delivery system 100 includes a therapeutic and/or surgical radiation source 105 to administer a prescribed radiation dose to a target volume in conformance with a treatment plan. Radiation treatment delivery system 100 may also include an imaging system 3020 (including imaging sources 120 and detectors 115) to capture inter-treatment images of a patient volume (including the target volume) for registration or correlation with the diagnostic images described above in order to position the patient with respect to the radiation source. Radiation treatment delivery system 100 may also include a digital processing system 3030 to control therapeutic radiation source 105, imaging system 3020, and a patient support device such as a treatment couch 110. Digital processing system 3030 may include one or more general-purpose processors (e.g., a microprocessor), special purpose processor such as a DSP or other type of device such as a controller or FPGA. Digital processing system 3030 may also include other components (not shown) such as memory, storage devices, network adapters and the like. Digital processing system 3030 may be coupled to therapeutic radiation source 105, imaging system 3020 and treatment couch 110 by a bus 3045 or other type of control and communication interface.

Figure 8:
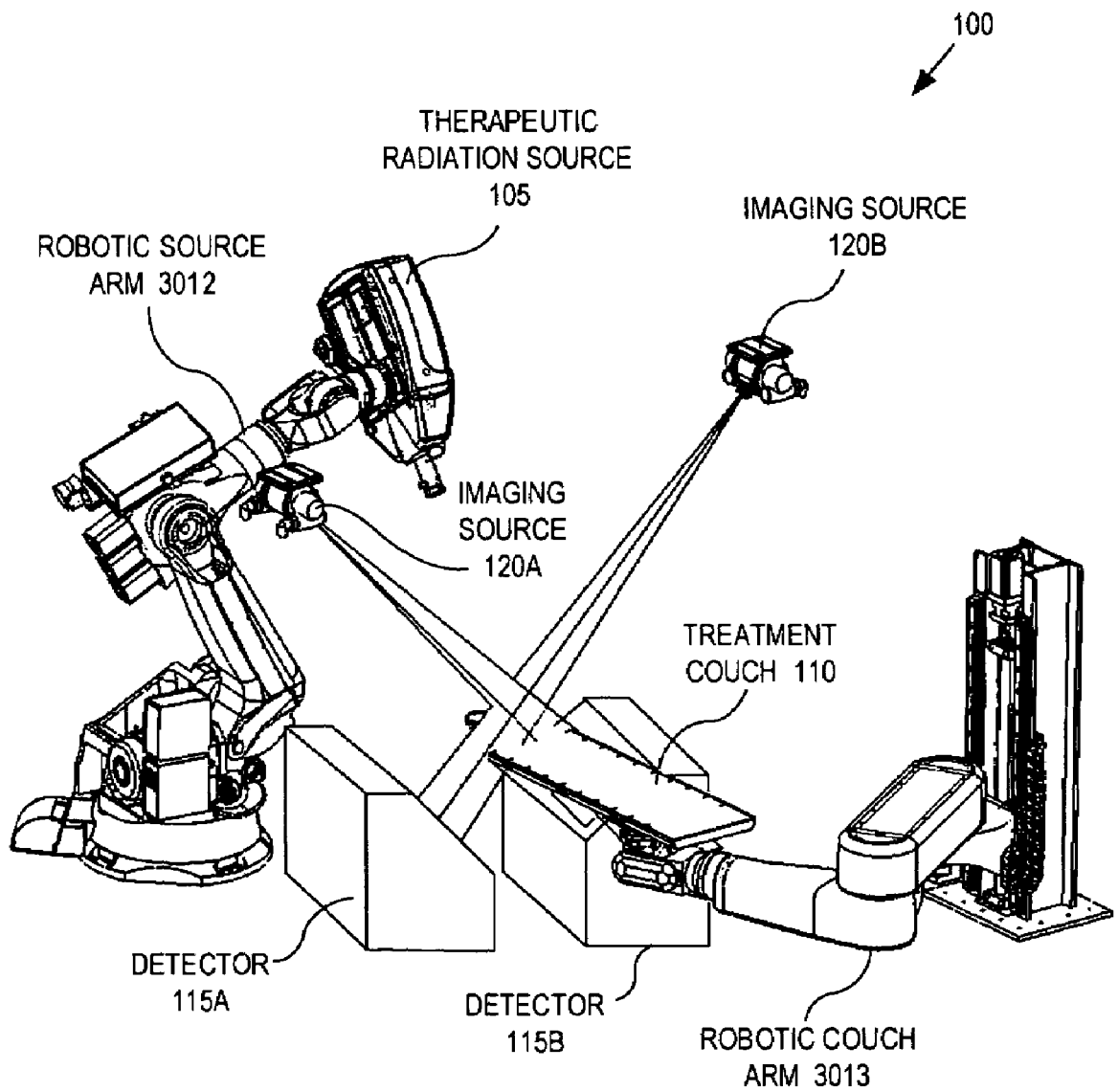
FIG. 8 is a perspective view of a treatment delivery system, in accordance with an embodiment of the invention.

FIG. 8 is a perspective view of a radiation treatment delivery system 100, in accordance with an embodiment of the invention. In one embodiment, radiation treatment delivery system 100 may be an image-guided, robotic-based radiation treatment system (e.g., for performing radiosurgery) such as the CyberKnife® system developed by Accuray, Inc. of California. In FIG. 8, therapeutic radiation source 105 may be a linear accelerator ("LINAC") mounted on the end of a robotic source arm 3012 having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With radiation treatment delivery system 100, in one embodiment, radiation beams may be delivered according to the treatment plan without fixing the patient to a rigid, external frame to register the intra-operative position of the target volume with the position of the target volume during the pre-operative treatment planning phase.

Imaging system 3020 (see FIG. 7) may be represented by imaging sources 120A and 120B and detectors (imagers) 115A and 115B in FIG. 8. In one embodiment, imaging sources 120A and 120B are X-ray sources. In one embodiment, for example, two imaging sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source. Alternatively, other numbers and configurations of imaging sources and detectors may be used.

Digital processing system 3030 may implement algorithms to register images obtained from imaging system 3020 with pre-operative treatment planning images in order to align the patient on the treatment couch 110 within the radiation treatment delivery system 100, and to precisely position the therapeutic radiation source 105 with respect to the target volume.

In the illustrated embodiment, treatment couch 110 is coupled to a robotic couch arm 3013 having multiple (e.g., 5 or more) degrees of freedom. Robotic couch arm 3013 may have five rotational degrees of freedom and one substantially vertical, linear degree of freedom. Alternatively, robotic couch arm 3013 may have six rotational degrees of freedom and one substantially vertical, linear degree of freedom or at least four rotational degrees of freedom. Robotic couch arm 3013 may be vertically mounted to a column or wall, or horizontally mounted to pedestal, floor, or ceiling. Alternatively, the treatment couch 110 may be a component of another mechanical mechanism, such as the Axum™ treatment couch developed by Accuray, Inc. of California, or be another type of conventional treatment table known to those of ordinary skill in the art. Robotic couch arm 3013 and treatment couch 110 may be referred to as a positioning system for a patient.

Alternatively, radiation treatment delivery system 100 may be another type of treatment delivery system, for example, a gantry based (isocentric) intensity modulated radiotherapy ("IMRT") system. In a gantry based system, a therapeutic radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method, comprising:
    positioning a quality assurance ("QA") marker at a preset position under guidance of an imaging guidance system of a radiation treatment delivery system;
    emitting a radiation beam from a radiation source of the radiation treatment delivery system at the QA marker, the radiation source for delivering radiation according to prescribed treatment plans;
    generating an exposure image of the QA marker due to the radiation beams, wherein the exposure image includes a beam exposure field, a center shadow cast by a central target of the QA marker, and a ring shadow cast about the center shadow by a ring target of the QA marker; and
    analyzing the exposure image to determine whether the radiation treatment delivery system is calibrated.

2. The method of claim 1, wherein the QA marker comprises:
    a housing being translucent to the radiation beam for housing the central target and the ring target.

3. The method of claim 2, wherein the QA marker includes two ring targets disposed in the housing, each of the two ring targets positioned to have a ring axis aligned with a trajectory passing through a center of the central target.

4. The method of claim 2, wherein the QA marker further comprises fiducials for tracking the QA marker, and wherein positioning the QA marker at the preset position under guidance of the imaging guidance system includes:
    tracking the fiducials of the QA marker with the imaging guidance system; and
    providing feedback to a positioning system of the radiation treatment delivery system to position the QA marker to the preset position based on the tracking.

5. The method of claim 4, wherein positioning the QA marker at the preset position under guidance of the imaging guidance system further includes:
    generating a reference image of the QA marker illustrating the fiducials using a first imaging modality; and
    registering the fiducials of the reference image with a real-time image of the fiducials generated by the imaging guidance system.

6. The method of claim 2, wherein analyzing the exposure image to determine whether the radiation treatment delivery system is calibrated comprises analyzing relative positions of one or more shadows and a beam exposure field in the exposure image.

7. The method of claim 6, wherein analyzing the exposure image to determine whether the radiation treatment delivery system is calibrated further comprises:
    analyzing the exposure image to determine centroids of a center shadow, a ring shadow, and a beam exposure field in the exposure image; and
    determining whether the centroids of the center shadow, the ring shadow, and the beam exposure field are concentrically aligned.

8. The method of claim 2, wherein analyzing the exposure image to determine whether the radiation treatment delivery system is calibrated comprises analyzing the exposure image to determine whether the radiation source, the imaging guidance system, and a treatment couch supporting the QA marker are aligned with each other.

9. The method of claim 1, wherein emitting the radiation beam from the radiation source comprises emitting a first radiation beam from the radiation source located at a first position and further comprising:
    translating the radiation source to a second position; and
    emitting a second radiation beam from the radiation source at the second position.

10. The method of claim 9, wherein generating the exposure image of the QA marker comprises generating a first exposure image of the QA marker due to the first radiation beam and further comprising:
    generating a second exposure image due to the second radiation beam; and
    analyzing the second exposure image to determine whether the radiation treatment delivery system is aligned.

11. The method of claim 10, wherein the first and second radiation beams have substantially orthogonal trajectories.

12. A radiation treatment delivery system, comprising:
    a positioning system to position an alignment target to a preset position;
    a detector;
    a therapeutic radiation source adjustably positioned to emit a radiation beam passing through the preset position and impingent upon the detector and,
    a quality assurance ("QA") marker positioned at the preset position, the QA marker including the alignment target to cast a first shadow on the detector within a beam exposure field of the radiation beam, a relative position of the first shadow and the beam exposure field for verifying alignment of the positioning system and the therapeutic radiation source;
    wherein the alignment target of the QA marker includes:
        a spherical target disposed within a housing of the QA marker to cast the first shadow on the detector in response to the radiation beam; and
        a first ring target disposed within the housing to cast a ring shadow on the detector in response to the radiation beam, wherein a ring axis of the first ring target is substantially aligned with a trajectory passing through a center of the spherical target, wherein the first ring target has a larger inner diameter than a diameter of the spherical target.

13. The radiation treatment delivery system of claim 12, further comprising an imaging source mounted to emit imaging signals at the preset position, the detector positioned to image the QA marker in response to the imaging signals, the positioning system to adjust a position of the QA marker in response to real-time feedback from the detector.

14. The radiation treatment delivery system of claim 12, wherein the alignment target further includes a second ring target disposed within the housing to cast a second ring shadow on the detector in response to a second radiation beam from the therapeutic radiation source, wherein a second ring axis of the second ring target is substantially aligned with a trajectory passing through a center of the spherical target.

15. The radiation treatment delivery system of claim 14, wherein the first and second ring axes are substantially perpendicular to each other and wherein the alignment target provides rotational and translational alignment validation therapeutic radiation source.

16. A machine-readable storage medium that provides instructions that, when executed by a therapeutic patient treatment system, will cause the therapeutic patient treatment system to perform operations comprising:

positioning a quality assurance ("QA") marker at a preset position under guidance of an imaging guidance system;

emitting a radiation beam from a radiation source at the QA marker;

capturing an exposure image of the QA marker due to the radiation beam wherein the exposure image includes a beam exposure field, a center shadow cast by a spherical target of the QA marker, and a ring shadow cast about the center shadow by a ring target of the QA marker; and analyzing the exposure image to determine whether a radiation treatment delivery system is aligned.

17. The machine-readable storage medium of claim 16, wherein analyzing the exposure image to determine whether the radiation treatment delivery system is aligned comprises analyzing a relative position of the beam exposure fields, the center shadow, and the ring shadow.

18. The machine-readable storage medium of claim 17, wherein analyzing the exposure image to determine whether the radiation treatment delivery system is aligned further comprises:

analyzing the exposure image to determine centroids of the center shadow, the ring shadow, and the beam exposure field; and determining whether the centroids of the center shadow, the ring shadow, and the beam exposure field are concentrically aligned.

* * * * *

UNITED STATES PATENT AND TRADEMARK OFFICE
CERTIFICATE OF CORRECTION

PATENT NO. : 7,356,120 B2  Page 1 of 1
APPLICATION NO. : 11/234708
DATED : April 8, 2008
INVENTOR(S) : William Main, Eric Earnst and Gopinath Kuduvalli It is certified that error appears in the above-identified patent and that said Letters Patent is hereby corrected as shown below:

Title Page;
In INID Code (54), and Col. 1, line 2, please replace "in" with --an--.

Signed and Sealed this

Twenty-second Day of July, 2008

JON W. DUDAS
*Director of the United States Patent and Trademark Office*